United States Patent
Sabo et al.

(10) Patent No.: US 8,196,590 B2
(45) Date of Patent: *Jun. 12, 2012

(54) VARIABLE MAGNETIC MOMENT MR NAVIGATION

(75) Inventors: Michael E. Sabo, Marissa, IL (US); Rogers C. Ritter, Charlottesville, VA (US); Roger N. Hastings, Plymouth, MN (US); Raju R. Viswanathan, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 991 days.

This patent is subject to a terminal disclaimer.

(21) Appl. No.: 12/145,419

(22) Filed: Jun. 24, 2008

(65) Prior Publication Data

US 2008/0319303 A1 Dec. 25, 2008

Related U.S. Application Data

(63) Continuation of application No. 10/834,579, filed on Apr. 29, 2004, now Pat. No. 7,389,778.

(60) Provisional application No. 60/467,683, filed on May 2, 2003.

(51) Int. Cl.
 *A61B 19/00* (2006.01)
 *A61M 35/00* (2006.01)
(52) U.S. Cl. ............................................. 128/899; 604/1
(58) Field of Classification Search .................. 128/899, 128/898, 897; 606/1, 2–38; 604/1–11; 600/410–415

See application file for complete search history.

(56) References Cited

U.S. PATENT DOCUMENTS

| | | | |
|---|---|---|---|
| 5,654,864 A | 8/1997 | Ritter et al. |
| 5,931,818 A | 8/1999 | Werp et al. |
| 6,014,580 A | 1/2000 | Blume et al. |
| 6,015,414 A | 1/2000 | Werp et al. |
| 6,128,174 A | 10/2000 | Ritter et al. |
| 6,148,823 A | 11/2000 | Hastings |
| 6,152,933 A | 11/2000 | Werp et al. |
| 6,157,853 A | 12/2000 | Blume et al. |
| 6,212,419 B1 | 4/2001 | Blume et al. |
| 6,216,026 B1 | 4/2001 | Kuhn et al. |
| 6,241,671 B1 | 6/2001 | Ritter et al. |
| 6,292,678 B1 | 9/2001 | Hall et al. |
| 6,296,604 B1 | 10/2001 | Garibaldi et al. |
| 6,298,257 B1 | 10/2001 | Hall et al. |
| 6,304,768 B1 | 10/2001 | Blume et al. |

(Continued)

OTHER PUBLICATIONS

Magnetic Manipulation Instrumentation for Medical Physics Research Authors: G. T. Gillies, r. C. Ritter, W. C. Broaddus, M. S. Grady, M. A. Howard, III, R. G. McNeil 1994 American Institute of Physics Rev. Sci. Instrum. vol. 65, No. 3, Mar. 1994 pp. 533-562.

(Continued)

*Primary Examiner* — Daniel L Robinson
(74) *Attorney, Agent, or Firm* — Harness, Dickey & Pierce, P.L.C.

(57) ABSTRACT

A method of navigating a medical device in an operating region in a subject. The method includes applying a magnetic field to the operating region and changing the magnetic moment of the medical device by selectively changing a physical condition of at least one magnet element in the medical device to change the orientation of the device with respect to the applied magnetic field.

15 Claims, 10 Drawing Sheets

U.S. PATENT DOCUMENTS

| | | |
|---|---|---|
| 6,304,769 B1 | 10/2001 | Arenson et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 * | 6/2002 | Garibaldi et al. ............ 128/899 |
| 6,428,551 B1 | 8/2002 | Hall et al. |
| 6,459,924 B1 | 10/2002 | Creighton, IV et al. |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al |
| 7,248,914 B2 | 7/2007 | Hastings et al. |
| 7,264,584 B2 | 9/2007 | Ritter et al. |
| 7,389,778 B2 | 6/2008 | Sabo et al. |
| 2001/0038683 A1 | 11/2001 | Ritter et al. |
| 2002/0019644 A1 | 2/2002 | Hastings et al. |
| 2002/0100486 A1 | 8/2002 | Creighton, IV et al. |
| 2002/0177789 A1 | 11/2002 | Ferry et al. |
| 2003/0125752 A1 | 7/2003 | Werp et al. |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0068173 A1 | 4/2004 | Viswanathan |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0033162 A1 | 2/2005 | Garibaldi et al. |
| 2005/0065435 A1 | 3/2005 | Rauch et al. |
| 2005/0096589 A1 | 5/2005 | Shachar |
| 2005/0113628 A1 | 5/2005 | Creighton, IV et al. |
| 2005/0113812 A1 | 5/2005 | Viswanathan et al. |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2005/0273130 A1 | 12/2005 | Sell |
| 2006/0004382 A1 | 1/2006 | Hogg et al. |
| 2006/0009735 A1 | 1/2006 | Viswanathan et al. |
| 2006/0025676 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036125 A1 | 2/2006 | Viswanathan et al. |
| 2006/0036163 A1 | 2/2006 | Viswanathan |
| 2006/0036213 A1 | 2/2006 | Viswanathan et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0061445 A1 | 3/2006 | Creighton, IV et al. |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0145799 A1 | 7/2006 | Creighton, IV |
| 2006/0270915 A1 | 11/2006 | Ritter et al. |
| 2006/0270948 A1 | 11/2006 | Viswanathan et al. |
| 2006/0278248 A1 | 12/2006 | Viswanathan |
| 2007/0016010 A1 | 1/2007 | Creighton, IV et al. |
| 2007/0016131 A1 | 1/2007 | Munger et al. |
| 2007/0019330 A1 | 1/2007 | Wolfersberger |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0030958 A1 | 2/2007 | Munger |
| 2007/0032746 A1 | 2/2007 | Sell |
| 2007/0038064 A1 | 2/2007 | Creighton, IV |
| 2007/0038065 A1 | 2/2007 | Creighton, IV et al. |
| 2007/0038074 A1 | 2/2007 | Ritter et al. |
| 2007/0038410 A1 | 2/2007 | Tunay |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0055130 A1 | 3/2007 | Creighton, IV |
| 2007/0060829 A1 | 3/2007 | Pappone |
| 2007/0060916 A1 | 3/2007 | Pappone |
| 2007/0060962 A1 | 3/2007 | Pappone |
| 2007/0060966 A1 | 3/2007 | Pappone |
| 2007/0060992 A1 | 3/2007 | Pappone |
| 2007/0062546 A1 | 3/2007 | Viswanathan et al. |
| 2007/0062547 A1 | 3/2007 | Pappone |
| 2007/0073288 A1 | 3/2007 | Hall et al. |
| 2007/0088197 A1 | 4/2007 | Garibaldi et al. |
| 2007/0135804 A1 | 6/2007 | Ritter |
| 2007/0137656 A1 | 6/2007 | Viswanathan |
| 2007/0146106 A1 | 6/2007 | Creighton, IV |
| 2007/0149946 A1 | 6/2007 | Viswanathan |
| 2007/0161882 A1 | 7/2007 | Pappone |
| 2007/0167720 A1 | 7/2007 | Viswanathan |
| 2007/0179492 A1 | 8/2007 | Pappone |
| 2007/0197899 A1 | 8/2007 | Ritter et al. |
| 2007/0197901 A1 | 8/2007 | Viswanathan |
| 2007/0197906 A1 | 8/2007 | Ritter |
| 2007/0225589 A1 | 9/2007 | Viswanathan |
| 2007/0250041 A1 | 10/2007 | Werp |
| 2007/0270686 A1 | 11/2007 | Ritter et al. |
| 2008/0004595 A1 | 1/2008 | Viswanthan |
| 2008/0006280 A1 | 1/2008 | Aliberto et al. |
| 2008/0015427 A1 | 1/2008 | Kastelein et al. ............ 600/410 |
| 2008/0015670 A1 | 1/2008 | Pappone ............ 607/122 |
| 2008/0016677 A1 | 1/2008 | Creighton, IV |
| 2008/0016678 A1 | 1/2008 | Creighton, IV et al. |
| 2008/0039705 A1 | 2/2008 | Viswanathan |
| 2008/0039830 A1 | 2/2008 | Munger et al. |
| 2008/0047568 A1 | 2/2008 | Ritter et al. |
| 2008/0055239 A1 | 3/2008 | Garibaldi et al. |
| 2008/0058608 A1 | 3/2008 | Garibaldi et al. |
| 2008/0058609 A1 | 3/2008 | Garibaldi et al. |

| | | |
|---|---|---|
| 2008/0058963 A1 | 3/2008 | Garibaldi et al. |
| 2008/0059598 A1 | 3/2008 | Garibaldi et al. |
| 2008/0064933 A1 | 3/2008 | Garibaldi et al. |
| 2008/0064969 A1 | 3/2008 | Kastelein |
| 2008/0065061 A1 | 3/2008 | Viswanathan |
| 2008/0077007 A1 | 3/2008 | Hastings et al. |
| 2008/0092993 A1 | 4/2008 | Creighton, IV |
| 2008/0097200 A1 | 4/2008 | Blume et al. |
| 2008/0114335 A1 | 5/2008 | Flickinger et al. |

OTHER PUBLICATIONS

Magnetic Materials for MEMS MRS Workshop on MEMS Materials Authors: Judy, et al. Apr. 2202 pp. 23-26.

New Magnetic Functionalities Presented by Prussian Blue Analogues Authors: Ohkoshi, et al. Fall 2002 pp. 34-38.

EFAB a New Approach to MEMS Fabrication Bang Nov. 2002 pp. 8.

* cited by examiner

VARIABLE MAGNETIC MOMENT MR NAVIGATION

This application is a divisional of U.S. patent application Ser. No. 10/834,579, filed Apr. 29, 2004, which is now U.S. Pat. No. 7,389,778, which issued Jun. 24, 2008, which claims priority of prior Provisional U.S. Application Ser. No. 60/467,683, filed May 2, 2003, the entire disclosure of which is incorporated herein by reference.

BACKGROUND OF THE INVENTION

This invention relates to the navigation of medical devices in magnetic fields, and in particular to the navigation of medical devices in magnetic resonance imaging equipment.

The navigation of a medical device in an operating region with the aid of an externally applied magnetic field, such as that provided by an MRI device, by using a controllable variable magnetic moment in the device tip has been proposed, and is in fact the subject of Kuhn, U.S. Pat. No. 6,216,026, Arenson, U.S. Pat. No. 6,304,769, and Hastings et al., U.S. Pat. No. 6,401,723. One way of creating a controllable variable magnetic moment in a medical device disclosed in these patents is through controlled variable currents in tiny coils in the distal end of the device, and preferably a set of at least three mutually perpendicular coils. However, it can be expensive to fabricate such coils and assemble them into the medical device. Furthermore, the magnetic field can cause significant heating of the long electrical leads to the coils.

SUMMARY OF THE INVENTION

The present invention provides navigation in magnetic fields with reduced reliance upon, or even the complete elimination of microcoils, and their attendant problems. A preferred embodiment of a medical device constructed according to the principles of this invention comprises at least one element of a material whose magnetization can be altered by changing a physical condition of the material. In accordance with the method of this invention a magnetic field is applied to an operating region in the patient. The magnetic moment of the medical device is selectively changed by changing a physical condition of at least one magnet element in the medical device to thereby change the orientation of the device with respect to the applied magnetic field.

In the preferred embodiment, the magnetic element has a Curie temperature in the range of normal body temperature, and the magnetization of the magnetic elements is controlled by raising and lowering the temperature of the magnetic element to selective reduce or increase the magnetism of the elements. However, the magnetic elements could be materials whose magnetism can be increased or decreased with other changes to the physical condition of the material, for example piezomagnetic materials whose magnetism changes with applied stress (or strain); optimagetic materials whose magnetism changes with applied light; electri-magnetic materials whose magnetism changes with applied electrical field

BRIEF DESCRIPTION OF THE DRAWINGS

Corresponding reference numerals indicate corresponding parts throughout the several view of the drawings.

DETAILED DESCRIPTION OF THE PREFERRED EMBODIMENT

Figure 1:
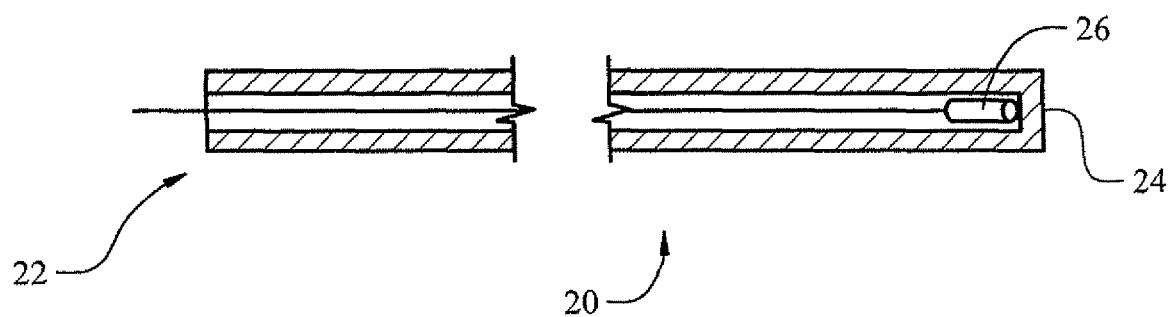
FIG. 1 is a schematic diagram of a medical device constructed according to the principles of this invention.
Figure 2:
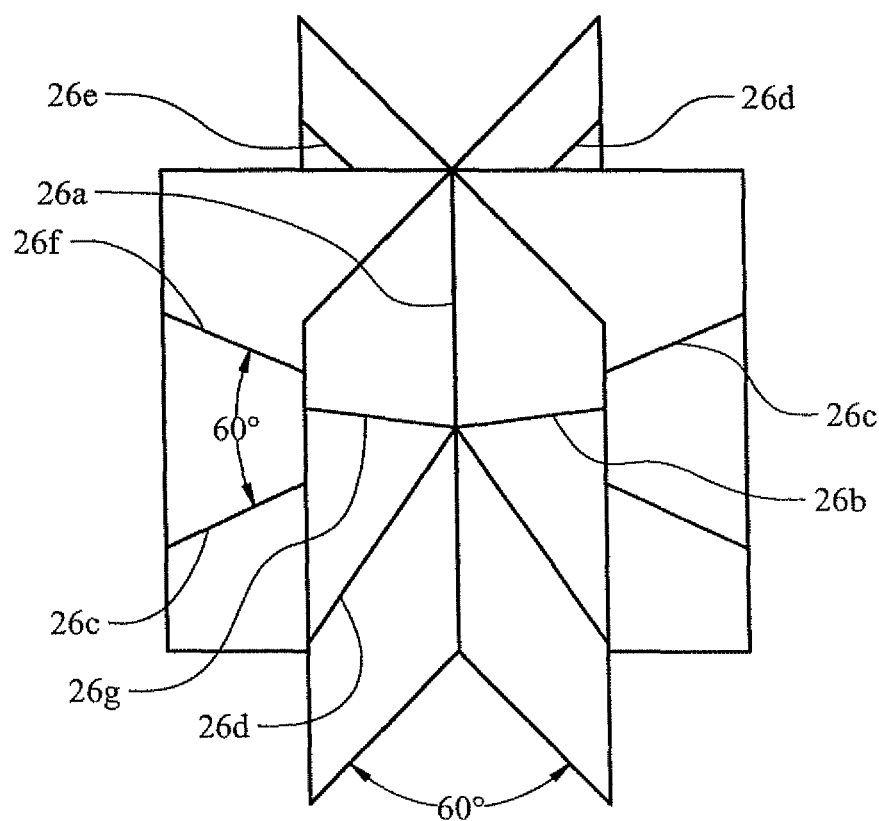
FIG. 2 is a schematic diagram of a possible arrangement of seven magnetic elements, showing the elements with a maximum separation of 60°.
Figure 3:
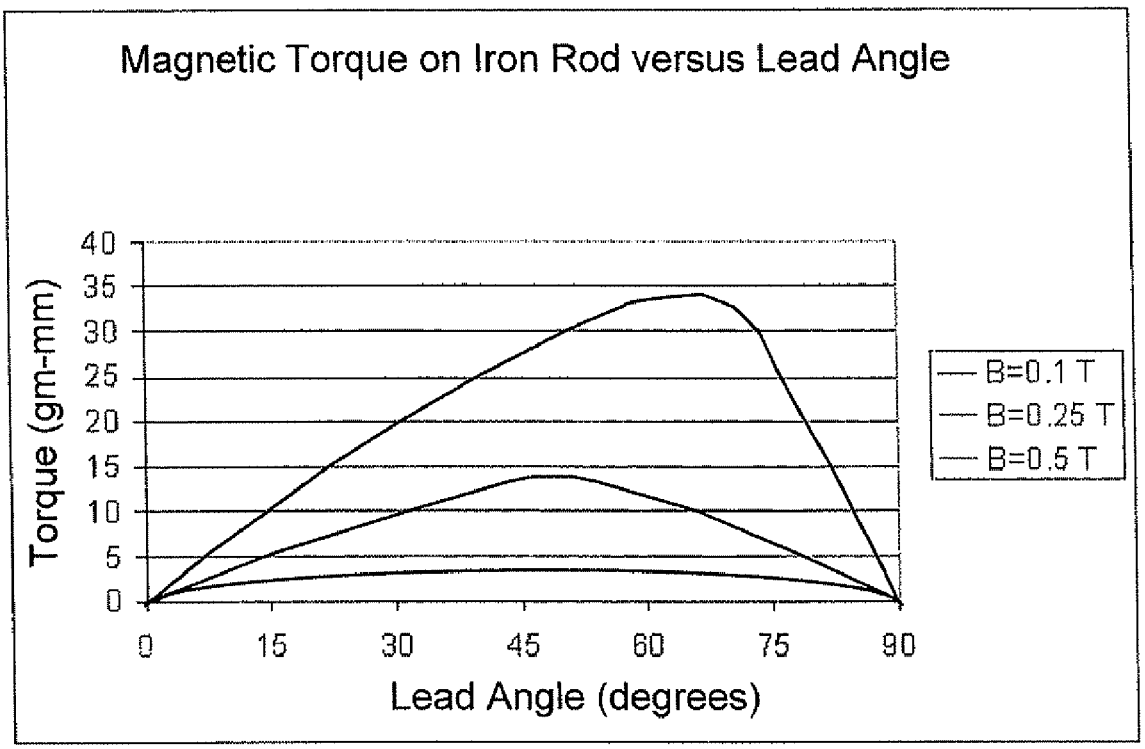
FIG. 3 is a graph of the alignment torque on an iron rod versus field lead angle.

A first embodiment of a medical device constructed according to the principles of this invention is indicated generally as 20 in FIG. 1. As shown in FIG. 1, the medical device 20 has a proximal end 22 and a distal end 24. The device 20 includes at least one, and in this preferred embodiment a plurality of, controllable magnetically responsive elements 26. One possible configuration of magnetically responsive elements 26 is shown in FIG. 2. As shown in FIG. 2, seven elements 26a-26g are arranged in the distal end of the medical device, with a maximum angular spacing of 60°.

While variable current flowing in a coil generates a variable magnetic moment, various embodiments of the present invention can include alternate elements 26 to generate variable magnet moment to supplement or replace coils within a medical device. In some embodiments the elements 26 preferably reduce or eliminate the heat generated by magnetic coils. In other embodiments the elements generate variable magnetic moments without the need for electrical conductors to avoid electrical heating of the electrical conductor lead wires by electric fields generated by the MRI imaging system.

There are a variety of materials whose magnetic properties can be selectively changed by changing a physical characteristic of the material for example by heating or cooling the material, by exposing the material to the light, or to an electric field. For example, thermomagnetic elements may be materials that have a Curie temperature on the order of magnitude of body temperature. Stimulated variable magnetization arises in materials due to alignment of atomic or molecular spins and/or to long range order in a crystal lattice. These alignments or orderings can be interrupted or broken by external stimuli, e.g. changes in physical condition. In a preferred embodiment, thermal stimulation or heating of the material reduces the magnetization of the material. Specifically, each magnetic material has a "Curie Temperature", $T_C$, above which a given material is non-magnetic. Materials can be engineered to have a Curie Temperature in a desired range. If a material's $T_C$ is somewhat higher than body temperature, then heating a material that resides within a catheter inside the body will reduce its magnetization. Similarly, if the material has a $T_C$ somewhat lower than body temperature, magnetization is increased by cooling the material. In either case, variable temperature gives rise to variable magnetic moment, which can be used to steer the catheter tip.

Opti-magnetic elements are materials whose magnetization can be altered by exposure to light. Recent research has focused on transparent or translucent magnetic materials that have magnetization altered by passing light of a given wavelength through the material. Such a material is discussed in Ohkoshi and Hashimoto, "New Magnetic Functionalities Presented by Prussian Blue Analogues", in The Electrochemical Society Interface, p. 34, (Fall 2002), incorporated herein by reference. These or other opti-magnetic materials will allow steering control through variable magnetic moments controlled by the application of varying light intensity supplied to the catheter tip, such as by fiber optic means.

Electri-magnetic materials are materials whose magnetization can be altered by the application of an electric field. Alterations in crystal structure can be induced in certain materials by the application of a static electric field across the material. It may be anticipated that materials may become available in which the application of a voltage (with little or no current), producing a DC electric field within the material, can enhance or reduce the material's magnetization.

Piezo-magnetic materials are materials whose magnetism can be altered by the application of stress (or strain) to the material. The change of magnetic properties with the application of a stress or strain is known as the Villari effect or the inverse magnetostriction effect or the inverse Joule effect. Stress or strain can be applied in a variety of ways, and can be either static or dynamic, the latter case including the acoustic application of force to the material (acouso-magnetic effect).

While variable current flowing in a coil generates a variable magnetic moment, alternate means are provided here to generate variable magnetic moment in materials contained within a device tip. An efficient means for moment variation that does not generate the heat associated with currents flowing in coils is needed. A preferred embodiment uses non-electric current means to generate the variable moment, to avoid electrical heating of the electrical conductor lead wires by rf electric fields generated by the MR imaging system. As disclosed herein a variable magnetic moment can be established in a medical device using temperature control of magnetic elements whose Curie temperature is close to body temperature.

Thermo-Magnetic Elements

In a preferred embodiment, the elements 26 are permeable magnetic materials near their $T_C$. Above the Curie temperature, these materials are non-magnetic. Below the Curie temperature, the magnetization of the material in an externally applied magnetic field increases as temperature decreases. In the strong magnetic fields of an MR imaging apparatus, the permeable material is saturated, and its saturation magnetization increases with decreasing temperature to its asymptotic saturation value. For ideal materials, the magnetization is about 80% of its saturation value when its absolute temperature is about 80% of the Curie temperature. Specialty materials have been formulated for specific applications that have much sharper Curie transitions (magnetization rises sharply as temperature falls below $T_C$).

The plurality of elements 26a-26g are nominally held at a temperature above the Curie temperature, $T_C$, so they are non-magnetic. During an interventional procedure in an MRI machine, the catheter tip is deflected by controllably reducing the temperature of one or more elements below $T_C$. Torques are exerted that tend to align the elements with the external MRI magnetic field. By controlling the temperature of the individual elements comprising the tip, a net tip magnetic moment is generated that can be oriented in any direction in space to steer the catheter tip.

For materials that have $T_C$ below body temperature, 37° C., the elements 26 are nominally non-magnetic. When it is desired to turn the medical device 20, one or more of the elements is cooled to a temperature below the Curie temperature to effect the turn. Since the elements are imaged in three dimensions by the MR imaging system, the proper element(s) 26a-26g can be selected for a turn specified by the physician on the MR image. The physician can control the element temperature via a joy stick or other input device. Alternatively, the physician can select the desired location or orientation of the tip, and the computer can control the element temperatures and simultaneously control the catheter advancer to achieve the desired result. Cooling can be achieved by passing an appropriate gas or liquid through a micro-tube within the catheter, exiting on or within the element. Gas exiting the micro-tube is cooled by expansion. A liquid that vaporizes upon exiting the tube cools the element in addition by the heat of vaporization. In addition, the liquid or gas may be pre-cooled. Temperature is controlled by controlling the gas or liquid flow velocity. Individual elements may be cooled by individual micro-tubes, or a single tube can be gated or switched in the distal catheter tip to address a selected element. A preferred element material with $T_C$ below body temperature is gadolinium, with a Curie temperature of 19° C. Gadolinium shows up well in an MR image, and is commonly used as a marker.

For materials that have $T_C$ above body temperature, optical fibers may be used to shine light on the elements to heat them above the Curie point. Nominally all elements would be heated above the Curie point. When it is desired to turn the medical device, heating is reduced to one or more of the elements to achieve the desired movement of the device tip. The temperature is controlled by controlling the light power. A fine wire thermocouple may be used to monitor and control temperature, however, a fiber optic micro-thermometer is preferred to avoid the need for electrical leads.

Alternate heating and cooling means could be provided. Where electrical lead wires are acceptable, or are made acceptable by shielding or interruption of the rf E-field standing waves, electrical heating/cooling may be considered. Heating is readily achieved using a resistor, which may be constructed from fine wire. Alternatively, electrical current, either dc or ac may be passed through the element itself, causing Ohmic heating within the element. In the latter case, it may be desirable to construct the element from fine wire made from the material to increase its electrical resistance. Cooling is achieved electrically with a Peltier-effect cooling chip.

In the above means, cooling is active and heating is passive (the element absorbs heat from its surroundings), or vice versa. It will be shown below that the volume of material in an element required to provide adequate catheter tip deflection is very small, and the amount of heat or energy required to raise or lower the element temperature is therefore very small. Therefore the element can be surrounded by a "leaky" thermal insulation layer adequate to avoid heating/cooling the surrounding body tissues during element heating/cooling, yet which conducts enough to allow the surrounding tissues to passively heat/cool the element with a reasonable time constant. It is estimated later that passive heat/cool times of less than one second can be achieved.

Alternatively, active cooling can be used simultaneously with active heating to achieve more rapid temperature control and thus rapid magnetic response. Active heating and cooling could employ a combination of fiber optic heaters and cooling fluid tubes. However, high efficiency, solid state, thermoelectric heater/coolers have become available and can be used to either heat or cool depending upon the direction of current flow through these Peltier effect devices. While current can be provided from a source outside the body through electrical lead wires, the use of laser energy, transmitted through the catheter by fiber optic means, and converted to current in the catheter tip through thermoelectric or photoelectric elements is also possible. Appropriate micro-chips can be fabricated that contain the photovoltaic cell and Peltier effect elements. If a micro-chip controller is provided, then a single fiber optic can be used to supply laser power that is converted to electrical energy in the catheter tip, which is in turn routed to the appropriate elements by the micro-controller. A separate optical communications fiber can be used to communicate with the micro-controller, however, the main beam can consist of pulses that are modulated to transfer data messages in addition to optical power through a single fiber optic.

The volume and dimensions of the elements 26 necessary to achieve a specified deflection angle of the medical device in an MRI magnetic field can be estimated for a given medical device. It is desirable that the deflection of medical devices in an MRI be comparable to the deflection of a medical device in a dedicated magnetic navigation system, for example an EP mapping and ablation catheter being navigated in a magnetic navigation system, such as the Niobe magnetic navigation system available from Stereotaxis, Inc., St. Louis, Mo. The elements 26 should provide equivalent deflection to this catheter in the MR magnetic field. Thus, the maximum aligning torque on one of the elements 26 is preferably at least equal to the maximum aligning torque of magnetic catheters in available magnetic navigation systems. The maximum aligning torque on a magnet element on a magnetic catheter in a magnetic navigation system (MNS) and the maximum aligning torque on an element in an MRI may be expressed as:

$$\tau_{max} = M_{catheter} B_{MNS} V_{EP} \text{MNS} \quad (1)$$

$$\tau_{max} = M_{Curie} B_{MRI} V_{Curie} / \sqrt{2} \text{MRI} \quad (2)$$

where M is the magnet magnetization, B is the applied field, and V is the magnet volume. The square root of two appears in the second equation because the maximum torque occurs when the element is oriented 45 degrees from the field direction (actually the peak is at a larger angle when the elements are saturated). Equating Eq. (1) and Eq. (2):

$$V_{Curie} = 1.414 * (M_{Catheter}/M_{Curie}) * (B_{MNS}/B_{MRI}) * V_{EP} \quad (3)$$

The measured magnetization of a Neo-45 catheter magnet is 1.2 Tesla, while a high quality permeable element (e.g., pure iron) can have a saturation magnetization of about 2 Tesla. The applied field in a magnetic navigation system is of the order of 0.1 Tesla, while it is expected that MR interventions will take place in 3 Tesla MRI machines to achieve image resolution adequate for navigation. Eq. (2) then gives:

$$V_{Curie} = V_{Catheter}/35 \quad (4)$$

Equation 4 shows that the elements 26 in an MRI can yield the same torque as the catheter magnet in a magnetic navigation system, but with about $1/35^{th}$ the volume. This is important since multiple elements must be used to achieve omni-directional tip moment in a single direction field. For a typical catheter magnet volume of 21.8 mm³, an element volume of only 0.62 mm³ supplies the equivalent magnetic torque in an MRI.

The dimensions of a suitable element 26 can be can be determined from the fact that the diameter of a conventional magnetically navigable catheter is about 2.5 mm (e.g., a magnetically guidable EP catheter available from Stereotaxis, Inc., St, Louis, Mo.). If the elements 26 are arranged at an angle of 30° with respect to diameter of the device, the maximum length of the elements 26 is 2.9 mm. Given the desired element volume of 0.62 mm³, the element dimensions are preferably:

d=0.52 mm

L=2.9 mm

V=0.62 mm³

L/d=5.6 (5)

The L/d ratio for the element is important in calculating the torque versus field angle function.

Permeable elements behave differently from permanent magnets in an external magnetic field. A permanent tip magnet will experience a torque that tends to align the magnet with the external field. This torque is in the same direction for all "lead angles" (or angles between the tip magnetic moment and applied field) between 0 and 180 degrees. A permeable element however, has no intrinsic magnetization direction, and either end of the element can align with a given pole of the external field. Thus the torque on an element is zero when the lead angle is 90 degrees, because the element is torqued equally to the North and South poles of the applied field. The peak torque on an element in an MRI occurs at a lead angle that depends upon the MRI element dimensions, and is about 70 degrees for the elements discussed above, decreasing rapidly to zero at 90 degrees. In a given plane, multiple elements are required to achieve continuous torque in a given direction. At first blush, it would appear that two elements are adequate in each of three orthogonal planes to achieve omni-directional steering. However, the rapid drop in torque above 70 degrees lead angle means that a dead zone of angles will exist for two elements.

As shown in FIG. 2, at least one symmetrical arrangement of elements exists in which three elements are placed in each of three planes with an angle of 60 degrees between planes. Pairs of elements may be activated to achieve torques about any given axis.

The torque on the elements increases with the square of the applied magnetic field before the element saturates, and increases linearly with the field thereafter. Below saturation, the peak torque occurs when the field angle leads the element axis angle by 45°. As the elements become more saturated, the torque continues to increase somewhat above the 45° angle, and peaks closer to 90° when the elements are fully saturated. The torque then falls rapidly to zero at 90°, and reverses direction for angles larger than 90°. Since the elements will almost certainly be saturated in the 3 Tesla field of the MRI, peak torques will occur closer to 90° lead angles. This is important for navigation. First, controlling torques over a larger range of angles than 0-45 degrees reduces requirements for image resolution and/or tip localization accuracy. Secondly, fewer elements are required, for example one element every 60 degrees instead of every 45 degrees for navigation, reducing the total number of elements required from nine to seven.

Convenient, closed form, estimates for the element torque are given below For closed form solutions, a simple two-branch model for the element B-H curve is used:

$$B = \mu \mu_0 H, \ H < B_S/\mu\mu_0$$

$$B = B_S, \ H < B_S/\mu\mu_0 \quad (6)$$

where $\mu$ is the element permeability, and $B_S$ is the element saturation induction. The torque on the element in an externally applied field is then:

$$\tau = \frac{(V \cdot B^2)}{2\mu_0}(\lambda_\parallel - \lambda_\perp)\sin(2\theta) \quad (7)$$

where:

$\lambda_i = \gamma_i$ when B<Bc $\lambda_i = \gamma_i B_c/B$ when B>$B_c$ (8)

where:

$B_c = B_s(\mu-1)/(\mu\sqrt{(\gamma_\parallel \cos(\theta))^2 + (\gamma_\perp \sin(\theta))^2})$ $\gamma_i = (\mu-1)/(1+(\mu-1)\beta_i)$ where τ=torque on the element in Nt-m
V=element volume in m³
B=magnitude of the applied magnetic field in Tesla
θ=angle between the element axis and the applied field, in radians
$\beta_i$=demagnetizing factor parallel or perpendicular to the element axis The demagnetizing factors can be found in tables or derived from formulas. They depend only upon the L/D ratio of the element. Equation (7) is evaluated versus lead angle for various applied fields in FIG. 4, and versus applied field for various lead angles in FIG. 5. The values $B_S$=2 Tesla, and μ=20 appropriate for iron were used in FIGS. 4 and 5, with element dimensions of 0.52 mm diameter by 3 mm length.

Figure 4:
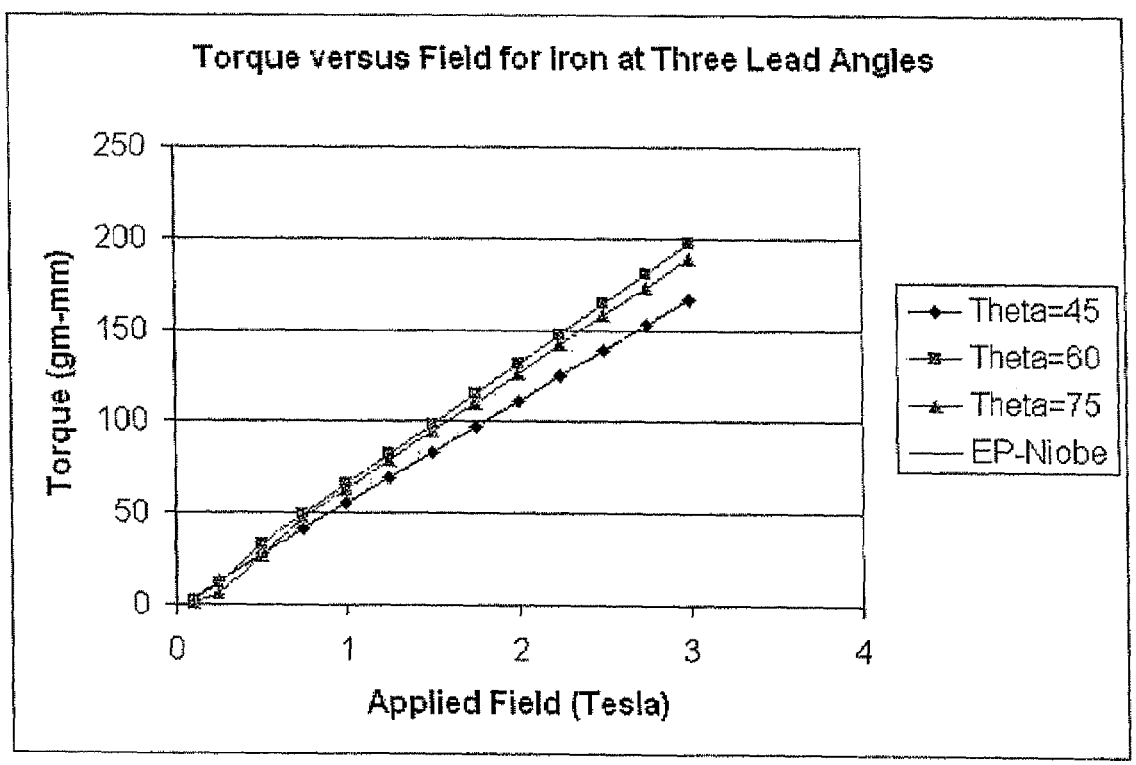
FIG. 4 is a graph of the torque on an iron rod versus applied magnetic field.
Figure 5:
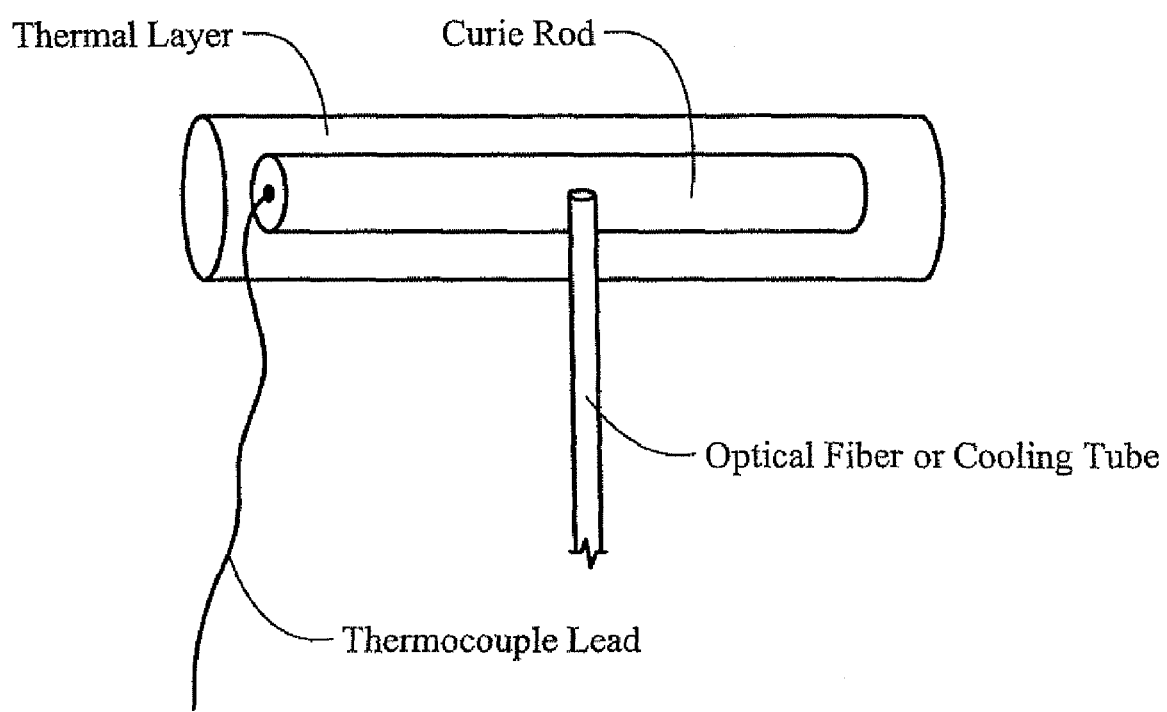
FIG. 5 is a schematic diagram of a curie element with thermal layer, heating (cooling) means, and thermocouple lead.

From FIG. 4 that the torque peaks at 45° lead angle in small fields, and peaks at larger lead angles as the element becomes saturated in larger fields. FIG. 5 plots the torque on this element versus applied field for various lead angles. The maximum torque on a catheter magnet in a magnetic navigation system at 0.1 Tesla is shown for comparison. A typical magnetic catheter tip magnet has magnetization of 1.2 Tesla and volume of 21.8 mm³, yielding a maximum magnetic torque of 212 gm-mm in a 0.1 Tesla applied field. For the element dimensions shown, the torque is equal to the catheter magnet torque at about 3 Tesla, as anticipated.

Heating and Cooling Times

Figure 6:
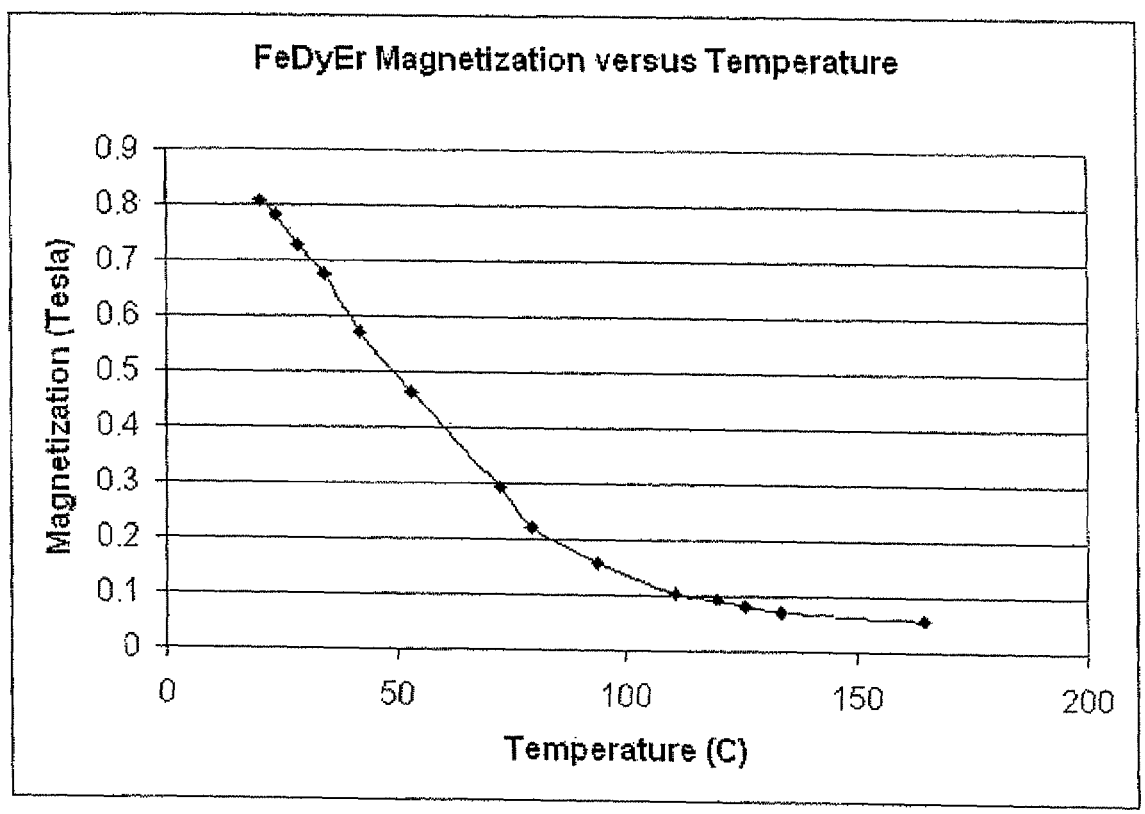
FIG. 6 is a graph of the magnetization of Curie element sample in 0.5 Tesla applied field.

To achieve navigation performance comparable to available magnetic navigation systems the elements must heat up and cool down in a few seconds. For example, an element heated by an optical fiber terminating at the center of the element (or a cooling tube in the same configuration). FIG. 6 shows an element and surrounding thermal layer chosen to give proper cooling rates. A thermocouple (or fiber optic thermometer) is shown for temperature control.

The thermal diffusion time, or time for heat to be conducted from the center of the element to the end of the element is given by:

$$\tau_d = (C\rho/\kappa)(L/2)^2 \quad (9)$$

where C is the element heat capacity, ρ is its density, and κ is the thermal conductivity.

Some typical values for iron, nickel, and their alloys are:

C≈0.1 cal/gm.° K.≈0.4 J/gm° K.
ρ≈8 gm./cm³
κ≈0.8 Watts/cm° K.
L=0.3 cm giving:

$$\tau_d \approx 0.1 \text{ seconds} \quad (10)$$

which is shorter than some magnet navigation system response times. This assumes that the heat leak through the thermal layer is small compared to the heating power.

For heated elements, the passive cooling time will depend upon the thermal conductivity of the thermal layer, which conducts heat through its thickness from the hot element to the outside at body temperature. For cooling, the thermal diffusion time is given by:

$$\tau_c = (C\rho/\kappa_t)(Dt/4) \quad (11)$$

where $\kappa_t$ is the thermal conductivity of the thermal layer, D is the element diameter, and t is the thickness of the thermal layer. Picking a thermal conductivity representative of insulating plastic materials, and a thickness of about 0.5 mm, which is close to the wall thickness of the current magnetic catheter shaft, and D=0.5 mm. Evaluating Eq. (11) results in:

$$\tau_c \approx 0.7 \text{ sec} \quad (12)$$

where:

$\kappa_t \approx 0.003$ Watts/cm° K.

The heating input power required to heat the element to ΔT≈100° C. above body temperature in the thermal diffusion time of 0.1 second, and the heat loss through the thermal layer when the element is heated to ΔT≈100° C. can be computed. The input power, neglecting the heat loss is given by:

$$P_{in} \approx C\rho V\Delta T/\tau_d \approx 0.15 \text{ Joules}/0.1 \text{ sec}=1.5 \text{ Watts} \quad (13)$$

and the heat loss through the thermal layer is:

$$P_{leak} = \kappa_t \pi DL\Delta T/t \approx 0.2 \text{ Watts} \quad (14)$$

This verifies that the heat loss is small compared to the input power, and that the heat loss of 0.2 Watts will remove the stored heat energy in the element of about 0.15 Joules in about 0.7 seconds. The rather large temperature rise of 100 degrees may not be required for some Curie materials. A smaller ΔT will reduce the input and heat leak power but will not change the heating and cooling times. Thus, it appears that active heating with passive cooling can control the element magnetization with an acceptably short time constant.

When active heating and cooling is employed, a very highly insulating jacket can be used, and heat is applied and removed through the thermo-electric device, using a conductive material in contact with blood as the heat reservoir. The tiny heat of 0.15 Joules, required to change the element temperature by 100° C., will not result in measurable change the blood temperature of the patient. If this were a concern, a separate heat reservoir could be supplied within the catheter tip, and the entire catheter tip could then be thermally insulated. With active heating/cooling, the catheter deflection response time would be on the order of 0.1 seconds.

Several materials with Curie temperatures near body temperature have been identified. One likely candidate material that was tested is Fe(74.1 wt %), Er(18.5 wt %), Dy(7.4 wt %). A small rectangular piece of this material was wrapped with a bi-filar heating coil and suspended from a force gauge above a 12"×12" permanent magnet in field of about 0.5 Tesla. The sample was in a water bath at room temperature. The sample magnetization was computed from the measured net magnetic force and the known field gradient at the position of the sample, and was found to be approximately 1 Tesla. This nominal value is smaller than iron, however, the magnetization value may be larger in a 3 T magnetic field. As is, the magnetization is large enough to be useful with slightly larger diameter elements. The force fell to zero as expected when the sample was heated, as shown in FIG. 6. Heating and cooling times were measured, and found to be slightly larger than predicted from Eqs. (9) and (11).

Other suitable materials for use as Curie elements are $Y_2Fe_{17}$, HoFe, and Pd(94%)Co(6%). These materials have Curie temperatures in the range 57° C. to 92° C., with a range of saturation magnetization values. In addition, Gadolinium (Gd) has a Curie temperature of 19° C., and is non-magnetic at body temperature (37° C.). At −59° C. the absolute temperature is 80% of the Curie absolute temperature, and most of the saturation magnetization should be recovered at this temperature. Gd has the advantage that it is non-magnetic at room and body temperature going into the patient. Thus, zero cooling/heating power is required until the first steering move is commanded.

Thus, stimulated variable magnetization is possible, and in particular the magnetic moment of a medical device can be controlled by controlling the temperature of elements made of materials having Curie temperature near body temperature, and is feasible for steering catheters in an MRI machine.

Figure 7:
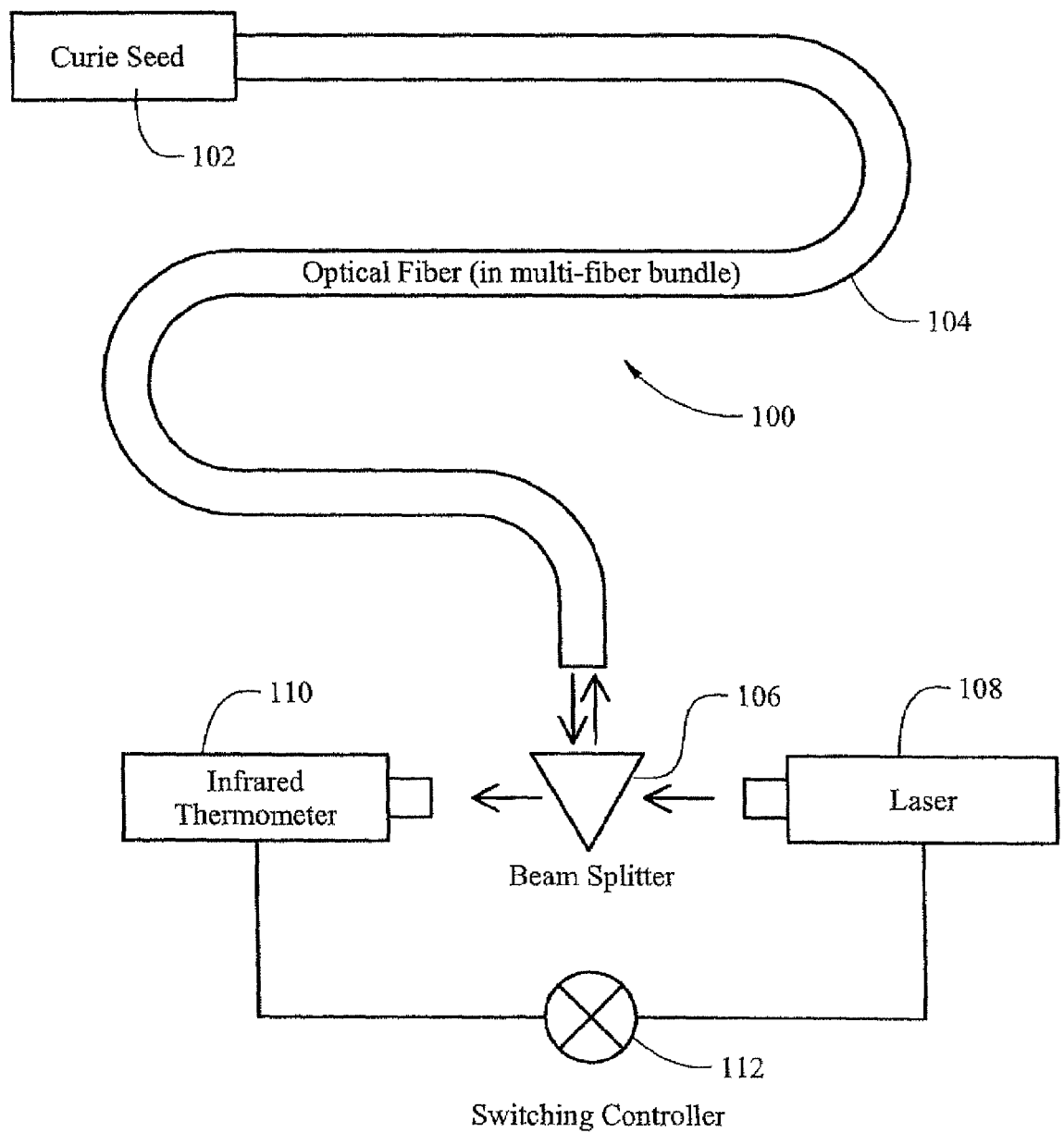
FIG. 7 is a schematic drawing of a device constructed according to the principles of this invention.
Figure 8:
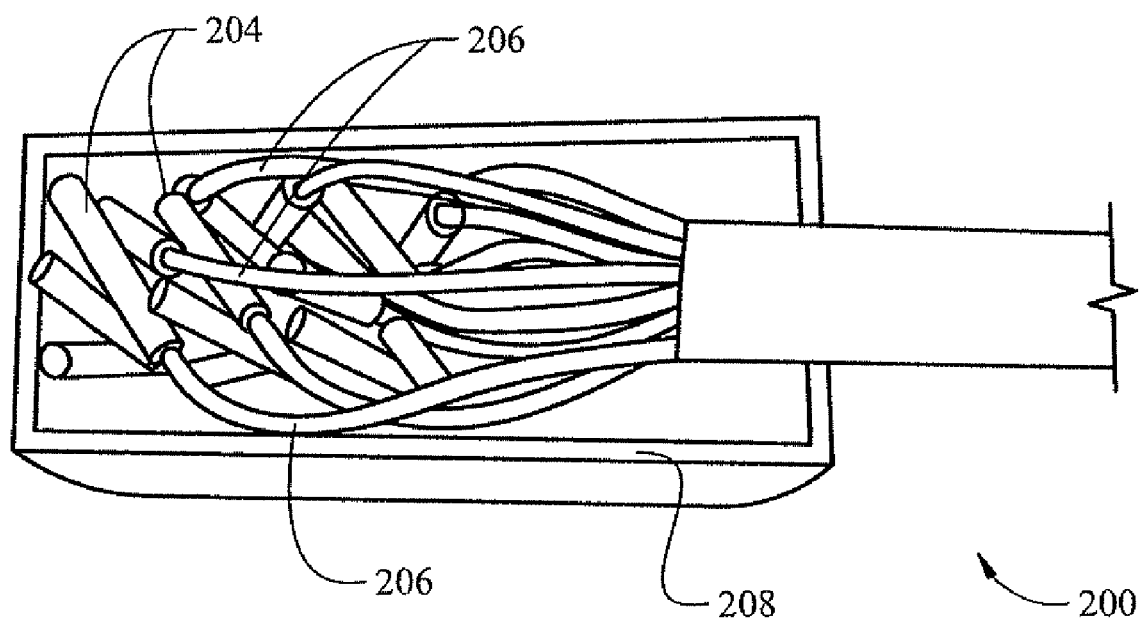
FIG. 8 is a side elevation view of the distal tip of a medical device constructed in accordance with the principles of this invention.
Figure 9:
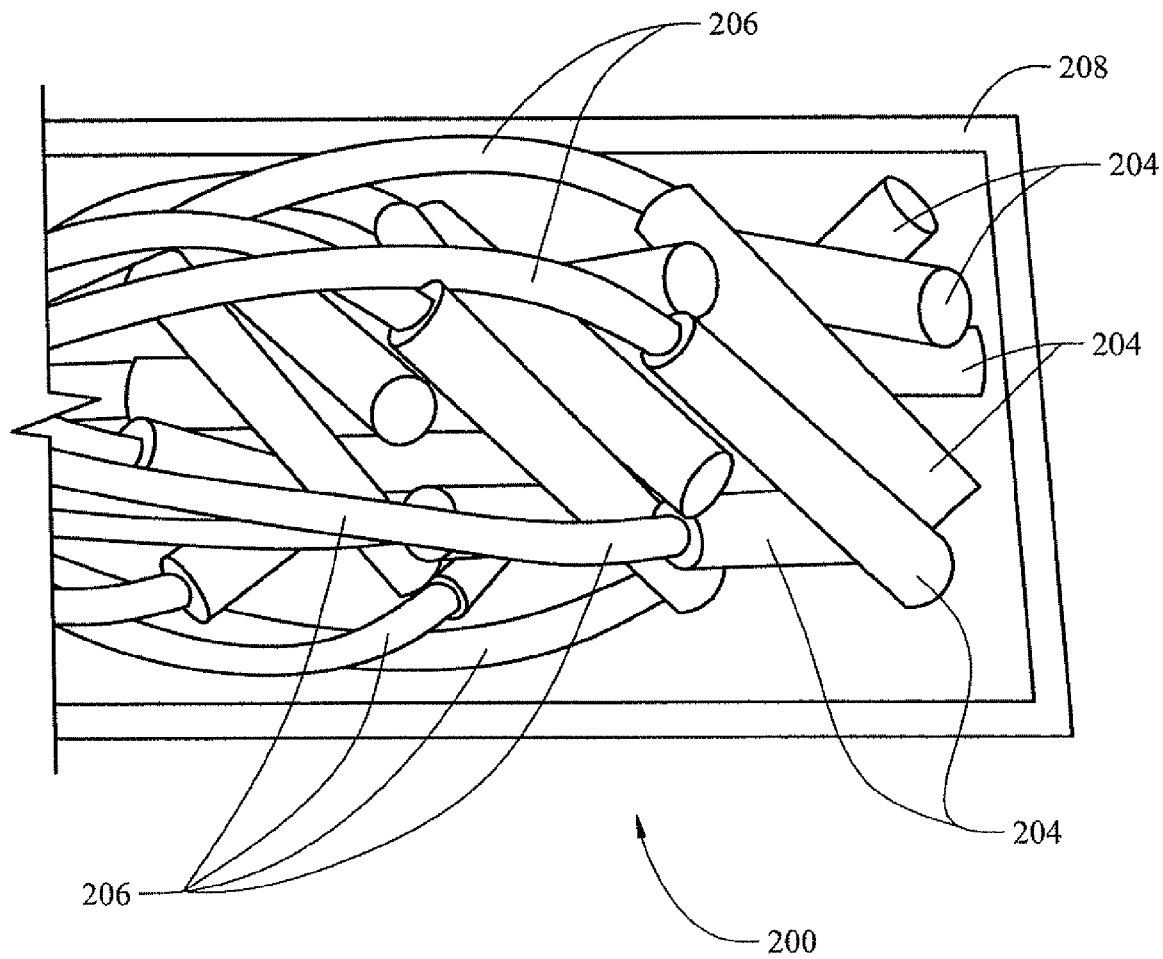
FIG. 9 is an enlarged side elevation view of the magnetic elements in the distal tip of the medical device.
Figure 10:
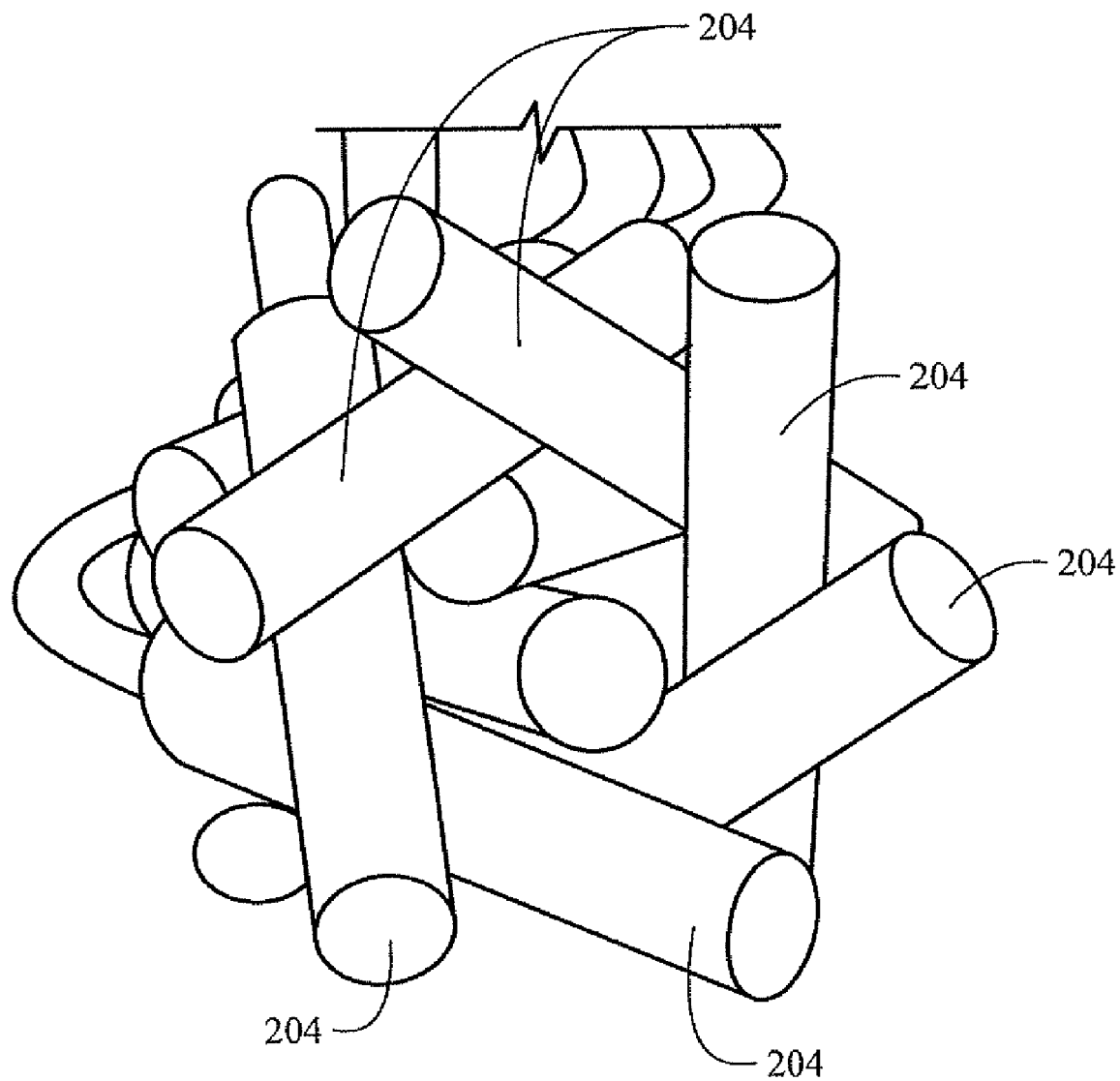
FIG. 10 is an enlarged end view of the magnetic elements in the distal tip of the medical device.
Figure 11:
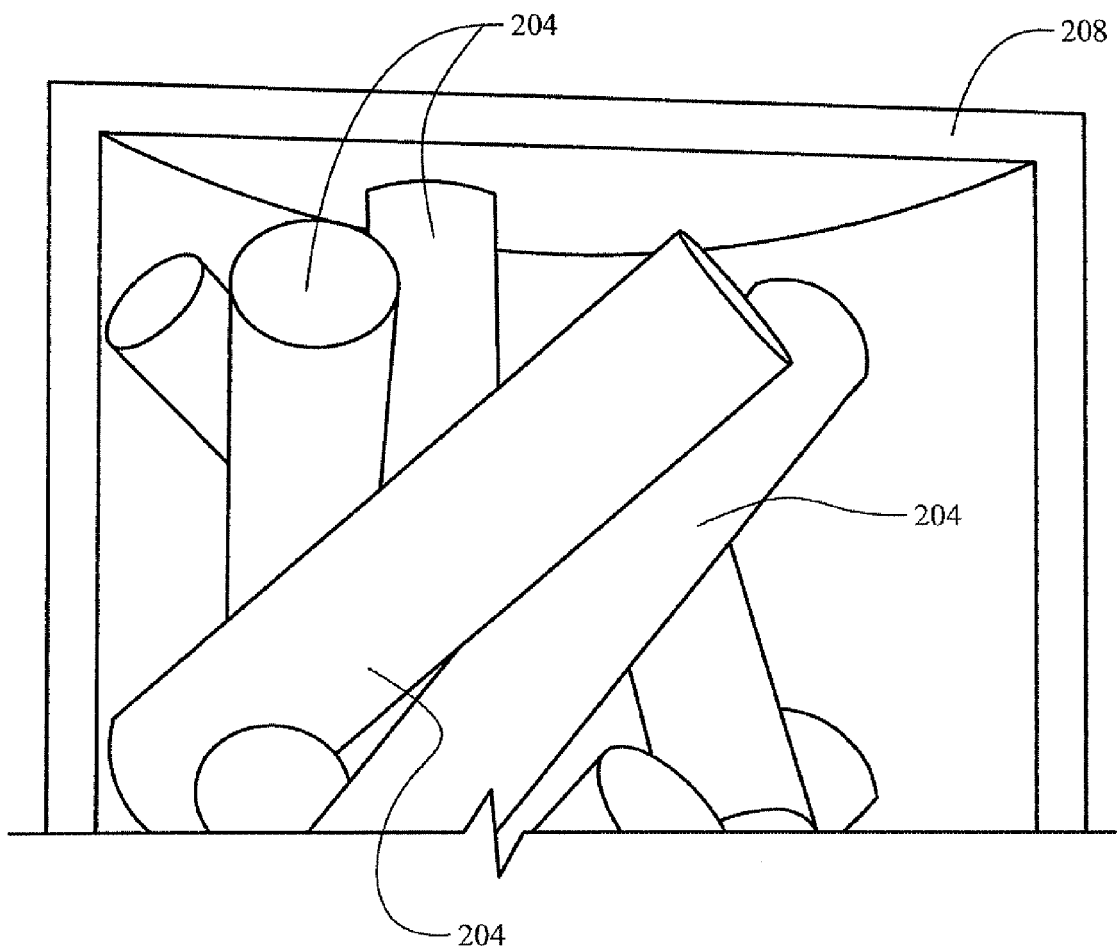
FIG. 11 is an enlarged side elevation view of one set of the magnetic elements in the distal tip of the medical device.

An embodiment of a device constructed according to the principles of this invention and useful in the methods of this invention is indicated generally as 100 in FIG. 7. The device 100 includes a magnetic element 102, preferably made of a ferromagnetic material in the shape of a cylinder. The magnetic characteristics of the material are selected for a desired Curie point and transition curve. One end of cylindrical magnetic element 102 is mated to the end of an optical fiber 104. Energy in the form of laser radiation is deposited at this interface when the laser is activated. The energy deposited raises the temperature of the element at the interface with the fiber. This energy is quickly conducted through the entire length of the element raising the temperature of the entire element. When the laser radiation is no longer applied, energy is lost from the seed through conduction into the surrounding material and radiation in the form of IR. Some of this IR is lost through the cylinder end that is mated to the optical fiber and can be measured at the opposite end.

An optical fiber 104, consisting of a glass or polymer fiber (one of many in a multi-fiber bundle) that is used to transmit radiation from one end of the fiber to the other with low transmission losses. One end of the fiber is mated to the end of the element 102 while the other is terminated at a beam splitter 106. The fiber 104 is used to transmit light from a laser 108 to the magnet element 102 and IR from the element surface to an infrared thermometer 110.

The beam splitter 106 is a special lens that is used to break a beam of light into two separate beams. This allows the light beam from the laser 108 to be directed onto the optical fiber 104 where it is delivered to the element 102. Returning IR from the element 102 is transmitted up the optical fiber 104 and through the beam splitter 106 where it is redirected to the infrared thermometer 110.

The laser 108 provides the energy used to heat the element 102 in the form of light (or laser radiation) via the beam splitter 106 and optical fiber 104. The operation of the laser 108 is cycled on and off at regular intervals with the length of the pulse during the "on cycle" determining the amount of energy deposited. Control of the cycling of the laser 108 is done by a dedicated switching controller 112.

The infrared thermometer 110 uses a sensor to measure IR radiation given off by a blackbody and converts it into a surface temperature measurement. IR radiation is transmitted from the element 102 to the sensor via an optical fiber 104 and beam splitting lens 106 during the "off cycle" of the laser 108. From this measurement a value of surface temperature is generated and sent to the switching controller 112.

The switching controller 112 preferably consists of a micro-controller board and software control algorithm. The board has two inputs; the temperature from the infrared thermometer 110 and a set-point value provided by an operator or external control device. The output of the device controls the on/off cycle of the laser 108. The control software can use a PID algorithm to compare the input temperature to the set-point temperature, as well as the rate-of-change in the input temperature. From this a calculated value of how much energy needs to be delivered during the next pulse is determined. The output of the board "cycles on" the laser 108 for a period of time necessary to deliver the calculated amount of energy. Another set of data is collected from the inputs when the laser 108 is cycled off, and the process repeats.

In another embodiment, separate optical fibers may be used to deliver energy to separate elements or sets of elements in the device. The orientation of the device tip in three dimensions may be controlled by separate heating or cooling of distinct elements or sets of elements, so that the tip can be arbitrarily oriented in space. In this case the switching controller 112 would also compute which elements to activate as well as their levels of activity, and appropriately direct energy into the corresponding optical fiber(s).

An embodiment of a medical device in accordance with the present invention, and useful with the methods of the present invention is indicated generally as 200 in FIGS. 8 through 11. The device 200 is preferably an elongate medical device, having a proximal end and a distal end 202. The medical device 200 could be a catheter, endoscope, or medical guide wire, or any other medical device that needs to be navigated within an operating region in a subject's body.

As shown in FIGS. 8-11 the device 200 comprises a plurality of magnetic elements 204. These elements are preferably arranged so that they are capable for creating a magnetic moment in any direction. As shown in the Figures, the elements 204 are arranged in three skewed, divergent cylindrical arrays of seven elements, comprising one generally axial element, and six surrounding elements. These elements are spaced at 60° intervals around the axial element, and are canted at an angle of 60° relative to the axial direction. Of course some other arrangement of elements 204 could be made. There are three arrays of elements to provide more mass than a singe array, and but there could be fewer or more arrays, if desired.

Each of the elements 204 is preferably made from a material having a Curie temperature that is in the range (i.e. within about 100° C.) of normal body temperature of 37° C. This range is desirable because these temperatures can be reached relatively quickly, and the heat can be dissipated relatively quickly, and it is relatively easy to shield surrounding body tissues from such temperatures. Examples of suitable materials include Gadolinium (Gd) and Manganese Arsenide (MnAs). Each element 202 is generally cylindrical, and may have a diameter of 0.5 mm and a length of about 2.5 mm. While the Curie elements can be incorporated into medical devices of any diameter by selecting the appropriate element dimensions, it is important to maintain a ratio of length to diameter for the elements that is large enough to provide adequate torque to the device. The torque on a sphere (length equal diameter) is zero. Element 202 preferably has length equal to or greater than five times its diameter. Smaller ratios of length to diameter are acceptable, but require a larger element volume to achieve a given desired torque.

A fiber optic lead 206 extends to each of the elements 204 for selectively conducting energy (light) to the element to heat it. The fiber optic lead 206 may, for example, be seated in a recess in the end of the element 204. Of course, other methods can be used for heating the elements 204, for example small resistance heating elements, heated fluid conductors, or Peltier heating/cooling elements. Electric current could also be applied directly to the elements 204 to heat them.

The fiber optic leads 206 may extend all the way to the proximal end of the device 200, or they may extend to a controller inside the device 200 that is optically or electrically powered, and which either selectively distributes or selectively generates optical energy to the elements 204 via leads 206, Control signals can be transmitted to the controller via a separate electric, or preferably fiberoptic line, or the control signals can be transmitted over the electric or optic power line.

The elements 204 are preferably disposed in a hollow, generally cylindrical shell 208 at the distal end of the device 200. The shell 208 may be made of platinum or a platinum-iridium alloy, or other suitable material. The shell is preferably sized and shaped, and made of materials compatible with use in a magnetic field, and in particular the magnetic field of an MI imaging device. The shell 208 preferably has an outside diameter of about 8 French (about 2.67 mm), and a length of about 6 mm.

In operation, the fiberoptic leads conduct sufficient light energy to all of the elements 204 so that the distal end of the device is non-magnetic. The device 200 can be easily introduced into the operating region in a subject without interference from either the magnetic field of a magnetic surgery system or the magnetic field of an MR imaging system. When the user desires to change the orientation of the device 200, the user can indicate the desired direction using an interface, which operates a computer controller to selectively interrupt the transmission of energy to selected elements 204. As the selected elements 204 cool, they regain the magnetism, creating a magnetic moment at the distal end of the device which interacts with the applied magnetic field (from either a magnetic surgery system or a MR imaging system) and changes the orientation of the distal end of the device. Because of the small size of the elements 204, they heat and cool relatively rapidly, so that the device 200 can be navigated in real time.

Some system for determining the location and/or orientation of the device is preferably provided to facilitate controllers identification of the elements 204 to "turn on" by allowing them to cool. Alternatively, if the elements are constructed of a material with a Curie temperature below normal body temperature, the elements 204 are normally off inside the body, and they are cooled to "turn on" or magnetize the element.

The Curie Temperature is a measure of the temperature at which the slope of the magnetization curve is a maximum, which for many materials is also the temperature at which magnetism disappears. However, it is not necessary to heat or cool materials to the Curie temperature for effective magnetization. A sufficient decrease in magnetization in some elements may occur as the material is heated without reaching the Curie temperature, and, similarly, the elements may not have to be cooled to completely restore magnetization in order to effectively navigate.

The elements 204 can be manufactured as a unit, building up the elements in their designed orientations in layers, using various Microelectromechanical System (MEMS) technologies, including for example EFAB marketing techniques available from MEMGen Corporation, Burbank, Calif. See, for example, Bang, EFAB, A New Approach to MEMS Fabrication. Sensors November 2002, and Judy et al., Magnetic Materials for MEMS, Jack W. Judy and Nosang Myung, "Magnetic Materials for MEMS", MRS Workshop on MEMS Materials, San Francisco, Calif., (Apr. 5-6, 2002), pp. 23-26. These technologies will allow magnetic element arrays to be inexpensively fabricated in batch processes, in sizes that can be incorporated into endoscopes, catheters, and even into guidewires.

What is claimed is:

1. A medical device navigable in an operating region in a subject using an externally applied magnetic field, the device including at least one element of a material whose magnetization can be altered by changing a physical condition of the material.

2. The medical device according to claim 1 further comprising means for changing the physical condition of the material.

3. A medical device navigable in an operating region in a subject using an externally applied magnetic field, the device including at least one element of a thermomagnetic material whose magnetization can be altered by a temperature change that is between 0°C. and 200°C.

4. The medical device according to claim 3 wherein the magnetization of the thermomagnetic material can be altered by a temperature change that is within 100° of body temperature.

5. The medical device according to claim 3 wherein the device includes an optomagnetic material whose magnetization can be altered by the application of light.

6. The medical device according to claim 3 wherein the device includes an piezomagnetic material whose magnetization can be altered by the application of pressure.

7. The medical device according to claim 3 wherein device includes an electri-magnetic element whose magnetization direction can be altered by the application of an electric field.

8. The medical device according to claim 3 wherein the device includes an piezomagnetic element whose magnetization direction can be altered by the application of mechanical stress.

9. The medical device according to claim 3 wherein the thermomagnetic material has a Curie temperature above normal body temperature, and further comprising means for selectively heating the at least one elements above the Curie temperature.

10. The medical device according to claim 3 wherein the thermomagnetic material has a Curie temperature below normal body temperature, and further comprising means for selectively cooling the at least one element below its Curie temperature.

11. The medical device according to claim 3 wherein the plurality of elements are arranged in at least skewed, divergent cylindrical array.

12. A medical device for navigation in an operating region in a subject to which a magnetic field is applied, the device comprising means for changing the magnetic moment at the distal end of the device.

13. A medical device for navigating in an operating region in a subject to which a magnetic field is applied, the device comprising at least one magnet element, and means for selectively changing a physical property of the at least one magnet element to change the magnetic moment of the device.

14. The device according to claim 13 wherein in the means for selectively changing the physical property of the at least one magnet element comprises means for heating the at least one magnet element.

15. The device according to claim 13 wherein in the means for selectively changing the physical property of the at least one magnet element comprises means for cooling the at least one magnet element.

* * * * *